US009714440B2

(12) United States Patent
Schalk et al.

(10) Patent No.: US 9,714,440 B2
(45) Date of Patent: *Jul. 25, 2017

(54) METHOD FOR PRODUCING PATCHOULOL AND 7-EPI-α-SELINENE

(71) Applicant: FIRMENICH SA, Geneva (CH)

(72) Inventors: Michel Schalk, Collonges-sous-Saleve (FR); Fabienne Deguerry, Geneva (CH)

(73) Assignee: FIRMENICH SA, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/577,475

(22) Filed: Dec. 19, 2014

(65) Prior Publication Data
US 2015/0099283 A1 Apr. 9, 2015

Related U.S. Application Data

(63) Continuation of application No. 13/695,840, filed as application No. PCT/IB2011/051991 on May 5, 2011, now Pat. No. 8,927,238.

(60) Provisional application No. 61/333,002, filed on May 10, 2010.

(30) Foreign Application Priority Data

May 10, 2010 (EP) .................... 10162433

(51) Int. Cl.
C12N 9/18 (2006.01)
C12P 15/00 (2006.01)
C12N 9/88 (2006.01)
C12N 15/82 (2006.01)
C12P 5/00 (2006.01)

(52) U.S. Cl.
CPC ............. C12P 15/00 (2013.01); C12N 9/88 (2013.01); C12N 15/8243 (2013.01); C12P 5/002 (2013.01); C12Y 402/0307 (2013.01)

(58) Field of Classification Search
CPC ........ C12N 9/18; C12N 15/8243; C12P 5/002
See application file for complete search history.

(56) References Cited

U.S. PATENT DOCUMENTS

| 6,468,772 | B1 | 10/2002 | Chappell et al. | 435/183 |
| 8,927,238 | B2 * | 1/2015 | Schalk | C12N 9/88 435/127 |
| 2006/0206957 | A1 | 9/2006 | Schalk | 800/278 |
| 2009/0205060 | A1 | 8/2009 | Schalk et al. | 800/13 |

FOREIGN PATENT DOCUMENTS

WO WO 00/17327 A2 3/2000
WO WO 2005/052163 A2 6/2005

OTHER PUBLICATIONS

International Search Report and Written Opinion of the International Searching Authority, application No. PCT/IB2011/051991, mailed Sep. 21, 2011.
Altschul et al., "Basic Local Alignment Search Tool," Journal of Molecular Biology, 215(3):403-410 (1990).
Altschul, "Amino Acid Substitution Matrices from an Information Theoretic Perspective," Journal of Molecular Biology, 219(3):555-565, (1991).
Bos et al., "Composition of the Essential Oil from Roots and Rhizomes of Valeriana wallichii DC," Flavour and Fragrance Journal, 12(2):123-131 (Mar. 1997).
Bouwmeester, "Engineering the essence of plants," Nature Biotechnology, 24(11):1359-1361, (Nov. 2006).
Deguerry et al., "The diverse sesquiterpene profile of patchouli, Pogostemon cablin, is correlated with a limited number of sesquiterpene synthases," Archives of Biochemistry and Biophysics, 454(2):123-136 (2006).
Keller et al., "Rapid synthesis of isoprenoid diphosphates and their isolation in one step using either thin layer or flash chromatography," Journal of Chromatography, 645(1):161-167 (1993).
Lücker et al., "Vitis vinifera terpenoid cyclases: functional identification of two sesquiterpene synthase cDNAs encoding (+)-valencene synthase and (−)-germacrene D synthase and expression of mono- and sesquiterpene synthases in grapevine flowers and berries," Phytochemistry, 65(19):2649-2659 (Oct. 2004).
Martin et al., "Engineering a mevalonate pathway in Escherichia coli for production of terpenoids," Nature Biotechnology, 21(7):796-802 (Jul. 2003).
Mathela et al., "Compositional Diversity of Terpenoids in the Himalayan Valeriana Genera," Chemistry & Biodiversity, 2(9):1174-1182 (Sep. 2005).
Schardl et al., "Design and construction of a versatile system for the expression of foreign genes in plants," Gene, 61(1):1-11 (1987).
Stemmer, "DNA shuffling by random fragmentation and reassembly: In vitro recombination for molecular evolution," Proc. Natl. Acad. Sci. USA, 91(22):10747-10751 (Oct. 1994).
Takahashi et al., "Metabolic Engineering of Sesquiterpene Metabolism in Yeast," Biotechnology and Bioengineering, 97(1):170-181 (May 2007).

(Continued)

Primary Examiner — Tekchand Saidha

(57) ABSTRACT

The present invention provides a method of producing patchoulol and 7-epi-α-selinene, said method comprising contacting at least one polypeptide with farnesyl phyrophosphate (FPP). In particular, said method may be carried out in vitro or in vivo to produce patchoulol and 7-epi-α-seline, compounds which can be useful in the field of perfumery. The present invention also provides the amino acid sequence of polypeptide useful in the method of the invention. A nucleic acid encoding the polypeptide of the invention and an expression vector containing said nucleic acid are also part of the present invention. A non-human host organism or a cell transformed to be used in the method of producing patchoul and 7-epi-α-selinene is also an object of the present invention.

7 Claims, 3 Drawing Sheets

(56) References Cited

OTHER PUBLICATIONS

Tatusova et al., "Blast 2 Sequences, a new tool for comparing protein and nucleotide sequences," FEMS Microbiology Letters, 174(2):247-250 (1999).

Wu et al., "Redirection of cytosolic or plastidic isoprenoid precursors elevates terpene production in plants," Nature Biotechnology, 24(11):1441-1447 (Nov. 2006).

Tuskan,G.A. et al., Hypothetical Protein POPTR_0015s09710g [Populus trichocarpa]., NCBI GenBank Accession No. XP_002321642, Dec. 31, 2013.

Zook,M.N., Putative vetispiradiene synthase 4 [Solanum tuberosum]., NCBI GenBank Accession No. AAD02269, Jul. 2, 1999.

\* cited by examiner

SEQUENCE LISTING

```
<160> NUMBER OF SEQ ID NOS: 11

<210> SEQ ID NO 1
<211> LENGTH: 553
<212> TYPE: PRT
<213> ORGANISM: Valeriana jatamansi

<400> SEQUENCE: 1

Met Leu Ser Thr Glu Ser Gln Val Phe Arg Pro Leu Ala Asn Phe Glu
1               5                   10                  15

Lys Ser Leu Trp Gly Asn Leu Phe Thr Ser Phe Ser Val Asp Tyr Leu
            20                  25                  30

Thr Lys Lys Thr Asn Thr Glu Glu His Glu Gly Leu Leu Glu Lys Val
        35                  40                  45

Arg Leu Met Phe Leu Asp Ala Ser Lys Leu Lys Ile Pro Glu Lys Ile
    50                  55                  60

Asn Phe Ile Asn Thr Leu Glu Arg Leu Gly Val Ser Tyr His Met Glu
65                  70                  75                  80

Arg Glu Ile Glu Asp Gln Leu His Gln Met Phe Asp Ala His Ser Lys
                85                  90                  95

Phe Gln Asp Asp Ile Gln Arg Phe Asp Leu Phe Thr Leu Gly Ile Tyr
            100                 105                 110

Phe Arg Ile Leu Arg Gln His Gly Tyr Asn Ile Ser Ser Asp Val Phe
        115                 120                 125

Lys Lys Leu Lys Asp Ser Asn Gly Lys Phe Lys Glu Glu Leu Lys Asp
    130                 135                 140

Asp Val Ile Gly Ile Leu Ser Leu Tyr Glu Ala Thr His Val Arg Thr
145                 150                 155                 160

His Gly Asp Asp Ile Leu Asp Glu Ala Phe Ile Tyr Thr Lys Ala Gln
                165                 170                 175

Leu Glu Ser Met Ser Thr Ala Ser Leu Ser Pro Phe Leu Gly Met Gln
            180                 185                 190

Val Thr His Ala Leu Ile Gln Ser Leu His Lys Gly Ile Pro Arg Ile
        195                 200                 205

Glu Ser Arg Asn Tyr Ile Ser Val Tyr Glu Glu Asp Pro Asn Lys Asn
    210                 215                 220

Asp Leu Leu Leu Arg Phe Ser Thr Ile Asp Phe Asn Leu Leu Gln Met
225                 230                 235                 240
```

| | | | | | | | | | | | |
|---|---|---|---|---|---|---|---|---|---|---|---|
|Leu|His|Lys|Gln|Glu|Leu|Cys|Asp|Ala|Ser|Arg|Trp Trp Asn Glu Met|

Leu His Lys Gln Glu Leu Cys Asp Ala Ser Arg Trp Trp Asn Glu Met
                245                 250                 255

Glu Phe Glu Thr Lys Leu Ser Tyr Ala Arg Asp Arg Val Val Glu Gly
            260                 265                 270

Tyr Leu Trp Thr Leu Ser Ala Tyr Tyr Glu Pro Lys Tyr Ser Leu Ala
            275                 280                 285

Arg Arg Ile Leu Ile Lys Leu Met Ile Leu Val Ser Leu Thr Asp Asp
290                 295                 300

Thr Tyr Asp Ala Tyr Gly Thr Leu Asp Glu Leu Gln Leu Phe Thr Asp
305                 310                 315                 320

Ala Val Glu Arg Leu Asp Glu Gly Ser Ile Asn Gln Leu Pro Asp Tyr
            325                 330                 335

Met Lys Ile Leu Tyr Lys Ala Leu Leu Asp Phe Phe Glu Glu Thr Glu
            340                 345                 350

Asp Ile Leu Cys Lys His Gly Ile Ile Asn Gly Ser His Arg Val Asn
            355                 360                 365

Tyr Gly Lys Tyr Val Tyr Lys Glu Ile Val Asn Cys Tyr Asn Thr Glu
            370                 375                 380

Tyr Lys Trp Phe Asn Lys Arg Tyr Val Pro Asp Phe Glu Glu Tyr Met
385                 390                 395                 400

Gln Lys Ala Val Val Thr Ser Gly Asn Asn Leu Leu Ile Thr Trp Ser
            405                 410                 415

Phe Gln Gly Met Asp Gln Val Ala Ser Ile Lys Ala Phe Glu Trp Val
            420                 425                 430

Lys Ser His Pro Lys Met Val Val Ser Ser Asn Lys Val Leu Arg Leu
            435                 440                 445

Val Asp Asp Val Met Ser His Glu Glu Glu Asp Glu Arg Gly His Val
450                 455                 460

Ala Thr Gly Leu Glu Cys Tyr Gln Lys Thr Tyr Gly Gly Asn Arg Lys
465                 470                 475                 480

Glu Ile Ile Pro Glu Phe Tyr Lys Arg Ile Asp Asp Ala Trp Lys Asp
            485                 490                 495

Val Asn Glu Glu Phe Leu Lys Pro Asp Lys Leu Pro Leu Glu Ile Leu
            500                 505                 510

Met Arg Val Ile Asn Leu Thr Arg Ile Gly Asp Val Val Tyr Lys Tyr
            515                 520                 525

Asp Asp Gly Tyr Thr His Pro Thr Lys Ala Leu Lys Asp His Ile Ile
530                 535                 540

Ser Leu Phe Val Asn Pro Ile Ile Ile
545                 550

<210> SEQ ID NO 2
<211> LENGTH: 1662
<212> TYPE: DNA
<213> ORGANISM: Valeriana jatamansi

<400> SEQUENCE: 2

```
atgttaagca ctgagagtca agttttttcgt ccgttggcaa attttgagaa agtttatgg     60 ggaaatcttt tcacctcatt ttctgtggat tatctgacta gaaaaacaaa tacagaagaa    120
catgaaggat tattagaaaa agtgagactg atgttttttag atgcatccaa attgaagatt    180
ccagaaaaga tcaatttcat aaatacactt gaaaggttag gtgtatcata tcatatggag    240
agagagattg aagatcagct tcatcagatg tttgatgctc attctaaatt tcaagatgat    300
attcaacggt tgatttgtt cactttggga atttacttca ggattctcag acaacatggt    360
```

-continued

```
tataatatct ctagcgatgt tttcaagaag ttgaaagata gcaatggaaa attcaaggaa    420
gaactaaaag atgatgtgat tggcattcta agcttgtatg aagctacaca tgtaagaacc    480
cacggtgacg atattctaga tgaagctttc atctatacaa aagctcaact agaatctatg    540
tccaccgcaa gtttaagccc gtttcttggt atgcaagtta cgcatgcttt gattcagtct    600
ctccacaaag ggatcccaag aatcgagtcg cgcaactata tatctgttta tgaagaagat    660
ccaaacaaaa atgatctatt attgaggttc tcaacgattg atttcaatct gctgcaaatg    720
cttcacaagc aagaattgtg tgatgcctca aggtggtgga atgaaatgga gtttgagacg    780
aaactatctt atgcgagaga tcgagtggta gaaggctatt tatggaccct tagcgcatat    840
tacgaaccga atactctttt ggctcgaaga atattaatca aattaatgat attggtatct    900
cttacggatg atacgtatga tgcatatggt acgttagatg aacttcaact ctttacggat    960
gcagtagaaa ggttggatga gggttccatc aatcagcttc ctgattacat gaagattctc   1020
tataaggctc tgctagattt tttcgaggaa acagaagata tattatgcaa acatggaata   1080
attaatggtt ctcatcgcgt taattatggg aaatatgtgt ataaagagat tgtgaattgc   1140
tacaataccg agtacaaatg gttcaacaaa agatacgtgc cggattttga agaatatatg   1200
cagaaagcag tagtgacttc aggtaacaat ttgcttataa cgtggtcttt tcaaggaatg   1260
gatcaagtcg caagtatcaa agcgttcgag tgggttaaaa gtcatccgaa atggtagtc    1320
tcgtcgaata aagtcctacg acttgttgac gacgtaatga gccacgagga agaagatgaa   1380
aggggacatg ttgcaacagg ccttgaatgc tatcagaaaa catatggtgg aaatagaaaa   1440
gagatcattc cagaattta taagaggatt gatgatgctt ggaaagatgt aaatgaagaa   1500
tttttgaaac ccgataaatt accgctagaa atactaatgc gtgttattaa cctcacgaga   1560
attggcgacg ttgtttacaa gtatgacgac gggtatactc atccaacgaa agcattaaag   1620
gatcacatca tatcgttgtt cgtgaatccc ataatcatat ga                      1662
```

```
<210> SEQ ID NO 3
<211> LENGTH: 29
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n is a, c, g, or t

<400> SEQUENCE: 3
gggawwgwnw bgttgaakkt tattttttgg                                    29

<210> SEQ ID NO 4
<211> LENGTH: 26
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n is a, c, g, or t

<400> SEQUENCE: 4
gtwscgtgng hgtcgtahgk gtcatc                                        26

<210> SEQ ID NO 5
```

```
<211> LENGTH: 25
<212> TYPE: DNA
<213> ORGANISM: Artificial sequence
<220> FEATURE:
<223> OTHER INFORMATION: Primer

<400> SEQUENCE: 5
acccttagcg catattacga accga                                         25

<210> SEQ ID NO 6
<211> LENGTH: 28
<212> TYPE: DNA
<213> ORGANISM: Artificial sequence
<220> FEATURE:
<223> OTHER INFORMATION: Primer

<400> SEQUENCE: 6
cgaaccgaaa tactctttgg ctcgaaga                                      28

<210> SEQ ID NO 7
<211> LENGTH: 28
<212> TYPE: DNA
<213> ORGANISM: Artificial sequence
<220> FEATURE:
<223> OTHER INFORMATION: Primer

<400> SEQUENCE: 7
ccactcgaac gctttgatac ttgcgact                                      28

<210> SEQ ID NO 8
<211> LENGTH: 28
<212> TYPE: DNA
<213> ORGANISM: Artificial sequence
<220> FEATURE:
<223> OTHER INFORMATION: Primer

<400> SEQUENCE: 8
cctcatccaa cctttctact gcatccgt                                      28

<210> SEQ ID NO 9
<211> LENGTH: 1979
<212> TYPE: DNA
<213> ORGANISM: Valeriana jatamansi

<400> SEQUENCE: 9
acgcggggga ctatcatata attaagagat taattaagtt tgtgaaaatg ttaagcactg    60
agagtcaagt ttttcgtccg ttggcaaatt ttgagaaaag tttatgggga aatcttttca   120
cctcattttc tgtggattat ctgactaaga aaacaaatac agaagaacat gaaggattat   180
tagaaaaagt gagactgatg tttttagatg catccaaatt gaagattcca gaaaagatca   240
atttcataaa tacacttgaa aggttaggtg tatcatatca tatggagaga gagattgaag   300
atcagcttca tcagatgttt gatgctcatt ctaaatttca agatgatatt caacggtttg   360
atttgttcac tttgggaatt tacttcagga ttctcagaca acatggttat aatatctcta   420
gcgatgtttt caagaagttg aaagatagca atggaaaatt caaggaagaa ctaaagatg    480
atgtgattgg cattctaagc ttgtatgaag ctacacatgt aagaacccac ggtgacgata   540
ttctagatga agctttcatc tatacaaaag ctcaactaga atctatgtcc accgcaagtt   600
taagcccgtt tcttggtatg caagttacgc atgctttgat tcagtctctc cacaagggga   660
tcccaagaat cgagtcgcgc aactatatat ctgtttatga agaagatcca aacaaaaatg   720
atctattatt gaggttctca aagattgatt tcaatctgct gcaaatgctt cacaagcaag   780
```

```
aattgtgtga tgcctcaagg tggtggaatg aaatggagtt tgagacgaaa ctatcttatg    840
cgagagatcg agtggtagaa ggctatttat ggacccttag cgcatattac gaaccgaaat    900
actctttggc tcgaagaata ttaatcaaat taatgatatt ggtatctctt acggatgata    960
cgtatgatgc atatggtacg ttagatgaac ttcaactctt tacggatgca gtagaaaggt   1020
tggatgaggg ttccatcaat cagcttcctg attacatgaa gattctctat aaggctctgc   1080
tagatttttt cgaggaaaca gaagatatat tatgcaaaca tggaataatt aatggttctc   1140
atcgcgttaa ttatggaaaa tatgtgtata aagagattgt gaattgctac aataccgagt   1200
acaaatggtt caacaaaaga tacgtgccgg attttgaaga atatatgcag aaagcagtag   1260
tgacttcagg taacaatttg cttataacgt ggtcttttca aggaatggat caagtcgcaa   1320
gtatcaaagc gttcgagtgg gttaaaaatc atccgaaaat ggtagtctcg tcgaataaag   1380
tcctacgact tgttgacgac gtaatgagcc acgaggaaga agatgaaagg ggacatgttg   1440
caacaggcct tgaatgctat cagaaaacat atggtggaaa tagaaaagag atcattccag   1500
aattttataa gaggattgat gatgcttgga aagatgtaaa tgaagaattt ttgaaacccg   1560
ataaattacc gctaaaaata ctaatgcgtg ttattaacct cacgagaatt ggcgacgttg   1620
tttacaagta tgacgacggg tatactcatc caacgaaagc attaaaggat cacatcatat   1680
cgttgttcgt gaatcccata atcatatgat tatcatcaat cgttcgacgt gtgtgcgcgt   1740
ggttttggtt aataagtaaa taaggtggac tgcatcacca tcccaaatct gcatgtttgc   1800
ttctgggttt ctttatttgt gtttgcgtgt ttacttgatt tcttttccgt tgtttgtaat   1860
aataccgagt atttcttttc cgttgtttgt aataatacgg agtatgcatt actctctttt   1920
tcacatgcaa ttaataagac gatattattt gtaaaaaaaa aaaaaaaaaa aaaaaaaa    1979
```

```
<210> SEQ ID NO 10
<211> LENGTH: 28
<212> TYPE: DNA
<213> ORGANISM: Artificial sequence
<220> FEATURE:
<223> OTHER INFORMATION: Primer

<400> SEQUENCE: 10
caccatgtta agcactgaga gtcaagtt                                        28

<210> SEQ ID NO 11
<211> LENGTH: 27
<212> TYPE: DNA
<213> ORGANISM: Artificial sequence
<220> FEATURE:
<223> OTHER INFORMATION: Primer

<400> SEQUENCE: 11
gataatcata tgattatggg attcacg                                         27
```

METHOD FOR PRODUCING PATCHOULOL AND 7-EPI-α-SELINENE

CROSS-REFERENCE TO RELATED APPLICATIONS

This application is a continuation of U.S. patent application Ser. No. 13/695,840 filed on Nov. 2, 2012, which is a 371 of International application no. PCT/IB2011/051991 filed on May 5, 2011, which claims the benefit of U.S. patent application No. 61/333,002 filed on May 10, 2010, which claims priority to European application no. 10162433.6 filed on May 10, 2010.

TECHNICAL FIELD

The present invention provides a method of producing patchoulol and 7-epi-α-selinene, said method comprising contacting at least one polypeptide with farnesyl phyrophosphate (FPP). In particular, said method may be carried out in vitro or in vivo to produce patchoulol and 7-epi-α-selinene, compounds which can be useful in the field of perfumery. The present invention also provides the amino acid sequence of a polypeptide useful in the method of the invention. A nucleic acid encoding the polypeptide of the invention and an expression vector containing said nucleic acid are also part of the present invention. A non-human host organism or a cell transformed to be used in the method of producing patchoulol and 7-epi-α-selinene is also an object of the present invention.

PRIOR ART

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Sesquiterpenes, for example, are widely found in the plant kingdom. Many sesquiterpene molecules are known for their flavor and fragrance properties and their cosmetic, medicinal and antimicrobial effects. Over 300 sesquiterpene hydrocarbons and 3000 sesquiterpenoids have been identified and many new structures are identified each year. Plant extracts obtained by different means such as steam distillation or solvent extraction are used as source of terpenes. Terpene molecules are often used as such, but in some cases chemical reactions are used to transform the terpenes into other high value molecules.

Biosynthetic production of terpenes involves enzymes called terpene synthases. There is virtually an infinity of sesquiterpene synthases present in the plant kingdom, all using the same substrate (farnesyl pyrophosphate, FPP) but having different product profiles. Genes and cDNAs encoding sesquiterpene synthases have been cloned and the corresponding recombinant enzymes characterized. The biosynthesis of terpenes in plants and other organisms has been extensively studied and is not further detailed in here.

Generally, the price and availability of plant natural extracts are dependent on the abundance, oil yield and geographical origin of the plants. In addition, the availability and quality of natural extracts is very much dependent on climate and other local conditions leading to variability from year to year, rendering the use of such ingredients in high quality perfumery very difficult or even impossible some years.

Valerian oil is one of these natural extracts. It is an aromatic oil, of which some components can advantageously be used in the field of perfumery and flavors. However, the purification of these individual constituents from the oil is not feasible at large scale.

A plant-independent method for producing the valerian oil constituents would therefore be very desirable but a cost-effective chemical synthesis of such compounds is so far not available.

Patchoulol and 7-epi-α-selinene are naturally occurring sesquiterpene molecules, which are useful in the field of perfumery and flavoring. A biochemical pathway leading to the synthesis of patchoulol and 7-epi-α-selinene would therefore be of great interest.

Analysis of the composition of *Valeriana jatamansi* oil showed that patchoulol was the major constituent of this oil. See for example Mathela C. S. et al. (2005), Chem. Biodivers. 2(9), 1174-1182 and Bos R. et al. Flay. Fragr. J. 12(2), 123-131. Nevertheless, this document does not provide or even suggest an amino acid or nucleotide sequence leading to the production of patchoulol and 7-epi-α-selinene.

A sesquiterpene synthase capable of synthesizing patchoulol has already been described in WO 2005/052163. A sesquiterpene synthase capable of synthesizing 7-epi-α-selinene synthase has been reported in Lucker et al (2004), Phytochemistry 65, 2649-2659. However, a sesquiterpene synthase capable of synthesizing both patchoulol and 7-epi-α-selinene has never been disclosed in the prior art.

The percentage of identity between the known sesquiterpene synthases and the polypeptide of the invention is very low. In particular, the patchoulol synthase described in WO 2005/052163 is only 39% identical to the sesquiterpene synthase of the invention. The closest protein sequence to the sesquiterpene synthase of the invention are a vetispiradiene synthase from *Solanum tuberosus* (NCBI accession No. AAD02269) and a predicted protein from *Populus trichocarpa* (NCBI accession n° XP_002321642 having both 49% identity with the present sesquiterpene synthase.

Despite extensive studies of terpene cyclization, the isolation and characterization of the terpene synthases is still difficult, particularly in plants, due to their low abundance, their often transient expression patterns, and the complexity of purifying them from the mixtures of resins and phenolic compounds in tissues where they are expressed.

It is an objective of the present invention to provide methods for making patchoulol and 7-epi-α-selinene in an economic way, as indicated above. Accordingly, the present invention has the objective to produce patchoulol and 7-epi-α-selinene while having little waste, a more energy and resource efficient process and while reducing dependency on fossil fuels. It is a further objective to provide enzymes capable of synthesizing patchoulol and 7-epi-α-selinene, which are useful as perfumery and/or aroma ingredients.

Abbreviations Used
bp base pair
BSA bovine serum albumin
cDNA complementary DNA
DNA deoxyribonucleic acid
dNTP deoxy nucleotide triphosphate
DTT dithiothreitol
FPP farnesyl pyrophosphate
GC gaseous chromatograph
IPTG isopropyl-D-thiogalacto-pyranoside
LB lysogeny broth
MOPSO 3-(N-morpholino)-2-hydroxypropanesulfonic acid
MS mass spectrometer
PCR polymerase chain reaction RMCE recombinase-mediated cassette exchange
3'-/5'-RACE 3' and 5' rapid amplification of cDNA ends
RNA ribonucleic acid
mRNA messenger ribonucleic acid

DESCRIPTION OF THE INVENTION

The present invention provides a method to biosynthetically produce patchoulol and 7-epi-α-selinene in an economic, reliable and reproducible way.

A "sesquiterpene synthase" or a "polypeptide having a sesquiterpene synthase activity" is intended here as a polypeptide capable of catalyzing the synthesis of a sesquiterpene molecule or of a mixture of sesquiterpene molecules from the acyclic terpene precursor FPP.

As a "patchoulol and 7-epi-α-selinene synthase" or as a "polypeptide having a patchoulol and 7-epi-α-selinene synthase activity", we mean here a polypeptide capable of catalyzing the synthesis of both patchoulol and 7-epi-α-selinene starting from FPP. Patchoulol and 7-epi-α-selinene may be the only products or may be part of a mixture with other sesquiterpenes.

The ability of a polypeptide to catalyze the synthesis of particular sesquiterpenes (for example patchoulol and 7-epi-α-selinene) can be simply confirmed by performing the enzyme assay as detailed in Example 2.

According to the present invention, polypeptides are also meant to include truncated polypeptides provided that they keep their sesquiterpene synthase activity as defined in any of the embodiments of the present invention and that they share at least the defined percentage of identity with the corresponding fragment of SEQ ID NO:1.

As intended herein below, "a nucleotide sequence obtained by modifying SEQ ID NO:2 or the complement thereof" encompasses any sequence that has been obtained by changing the sequence of SEQ ID NO:2 or of the complement thereof using any method known in the art, for example by introducing any type of mutations such as deletion, insertion or substitution mutations. Examples of such methods are cited in the part of the description relative to the variant polypeptides and the methods to prepare them.

The percentage of identity between two peptidic or nucleotidic sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for the purpose of determining the percentage of amino acid or nucleic acid sequence identity can be achieved in various ways using computer programs and for instance publicly available computer programs available on the worldwide web. Preferably, the BLAST program (Tatiana et al, *FEMS Microbiol Lett.*, 1999, 174:247-250, 1999) set to the default parameters can be used to obtain an optimal alignment of peptidic or nucleotidic sequences and to calculate the percentage of sequence identity.

One object of the present invention is therefore a method for producing patchoulol and 7-epi-α-selinene comprising
a) contacting FPP with at least one polypeptide having a patchoulol and 7-epi-α-selinene synthase activity and comprising an amino acid sequence at least 50% identical to SEQ ID NO:1;
b) optionally, isolating the patchoulol and the 7-epi-α-selinene produced in step a).

According to a preferred embodiment, the method is a method for producing patchoulol and 7-epi-α-selinene as the major products. According to an even more preferred embodiment, patchoulol and 7-epi-α-selinene represent altogether at least 50%, preferably at least 60%, preferably at least 70%, preferably at least 80%, preferably at least 90% of the product produced by the method of the invention.

According to another embodiment of the invention, 7-epi-α-selinene is the major product and patchoulol is the second major product. For example, 7-epi-α-selinene can represent at least 20%, preferably at least 30%, preferably at least 34% of the product obtained by the method of the invention. As another example, patchoulol can represent at least 10%, preferably at least 15%, preferably at least 16% of the product obtained by the method of the invention.

According to a preferred embodiment, the product of the method of the present invention further comprises at least one compound selected from the group consisting of germacrene A, α-guaiene, α-humulene, α-selinene, seychellene, α-patchoulene, α-bulnesene and (E)-nerolidol, these compounds being defined by the way of their structure as depicted in FIG. 1. In a more preferred embodiment, the product of the method of the present invention comprises all of these compounds.

The method can be carried out in vitro as well as in vivo, as will be explained in details further on.

The polypeptide to be contacted with FPP in vitro can be obtained by extraction from any organism expressing it, using standard protein or enzyme extraction technologies. If the host organism is an unicellular organism or cell releasing the polypeptide of the invention into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

The polypeptide having a patchoulol and 7-epi-α-selinene synthase activity, either in an isolated form or together with other proteins, for example in a crude protein extract obtained from cultured cells or microorganisms, may then be suspended in a buffer solution at optimal pH. If adequate, salts, BSA and other kinds of enzymatic co-factors, may be added in order to optimize enzyme activity. Appropriate conditions are described in more details in the Examples further on.

The precursor FPP may then be added to the suspension or solution, which is then incubated at optimal temperature, for example between 15 and 40° C., preferably between 25 and 35° C., more preferably at 30° C. After incubation, the patchoulol and 7-epi-α-selinene, and optionally the other sesquiterpene by-products produced may be isolated from the incubated solution by standard isolation procedures, such as solvent extraction and distillation, optionally after removal of polypeptides from the solution.

According to another preferred embodiment, the method of any of the above-described embodiments is carried out in vivo. In this case, step a) comprises cultivating a non-human host organism or cell capable of producing FPP and transformed to express at least one polypeptide comprising an amino acid sequence at least 50% identical to SEQ ID NO:1 and having a patchoulol and 7-epi-α-selinene synthase activity, under conditions conducive to the production of patchoulol and 7-epi-α-selinene.

According to a more preferred embodiment, the method further comprises, prior to step a), transforming a non human organism or cell capable of producing FPP with at least one nucleic acid encoding a polypeptide comprising an amino acid sequence at least 50% identical to SEQ ID NO:1 and having a patchoulol and 7-epi-α-selinene synthase activity, so that said organism expresses said polypeptide.

These embodiments of the invention are particularly advantageous since it is possible to carry out the method in vivo without previously isolating the polypeptide. The reaction occurs directly within the organism or cell transformed to express said polypeptide.

According to a particular embodiment of the invention, the at least one nucleic acid encoding the patchoulol and 7-epi-α-selinene synthase comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2 or the complement thereof. According to an even more preferred embodiment, said nucleic acid comprises the nucleotide sequence SEQ ID NO:2 or the complement thereof. In a most preferred embodiment, said nucleic acid consists of SEQ ID NO:2 or the complement thereof.

According to a preferred embodiment the at least one nucleic acid used in any of the above embodiments comprises a nucleotide sequence that has been obtained by modifying SEQ ID NO:2 or the complement thereof. According to an even more preferred embodiment, said at least one nucleic acid consists of a nucleotide sequence that has been obtained by modifying SEQ ID NO:2 or the complement thereof.

According to another embodiment, the at least one nucleic acid is isolated from *Valeriana jatamansi*.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells as specific objects of the present invention and in the examples.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art. Such methods can for example be found in the literature, for example in the following publications Martin, V. J., Pitera, D. J., Withers, S. T., Newman, J. D., and Keasling, J. D. Nat Biotechnol., 2003, 21(7), 796-802 (transformation of *E. coli*); Wu, S., Schalk, M., Clark, A., Miles, R. B., Coates, R., and Chappell, J., *Nat Biotechnol.*, 2006, 24(11), 1441-1447 (transformation of plants); Takahashi, S., Yeo, Y., Greenhagen, B. T., McMullin, T., Song, L., Maurina-Brunker, J., Rosson, R., Noel, J., Chappell, J, *Biotechnology and Bioengineering*, 2007, 97(1), 170-181 (transformation of yeast).

To carry out the invention in vivo, the host organism or cell is cultivated under conditions conducive to the production of patchoulol and 7-epi-α-selinene. Accordingly, if the host is a transgenic plant, optimal growth conditions are provided, such as optimal light, water and nutrient conditions, for example. If the host is a unicellular organism, conditions conducive to the production of patchoulol and 7-epi-α-selinene may comprise addition of suitable cofactors to the culture medium of the host. In addition, a culture medium may be selected, so as to maximize patchoulol and 7-epi-α-selinene synthesis. Optimal culture conditions are described in a more detailed manner in the following examples.

Non-human host organisms suitable to carry out the method of the invention in vivo may be any non-human multicellular or unicellular organisms. In a preferred embodiment, the non-human host organism used to carry out the invention in vivo is a plant, a prokaryote or a fungus. Any plant, prokaryote or fungus can be used. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism used to carry out the method of the invention in vivo is a microorganism. Any microorganism can be used but according to an even more preferred embodiment said microorganism is a bacteria or yeast. Most preferably, said bacteria is *E. coli* and said yeast is *Saccharomyces cerevisiae*.

Some of these organisms do not produce FPP naturally. To be suitable to carry out the method of the invention, these organisms have to be transformed to produce said precursor. They can be so transformed either before the modification with the nucleic acid described according to any of the above embodiments or simultaneously, as explained above.

Isolated higher eukaryotic cells can also be used, instead of complete organisms, as hosts to carry out the method of the invention in vivo. Suitable eukaryotic cells may be any non-human cell, but are preferably plant or fungal cells.

According to a preferred embodiment, the at least one polypeptide having a patchoulol and 7-epi-α-selinene synthase activity used in any of the above-described embodiments or encoded by the nucleic acid used in any of the above-described embodiments comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1. According to a more preferred embodiment, said polypeptide comprises the amino acid sequence SEQ ID NO:1. In an even more preferred embodiment, said polypeptide consists of SEQ ID NO:1.

According to another preferred embodiment, the at least one polypeptide having a patchoulol and 7-epi-α-selinene synthase activity used in any of the above-described embodiments or encoded by the nucleic acid used in any of the above-described embodiments comprises an amino acid sequence that is a variant of SEQ ID NO:1 obtained by genetic engineering. In other terms, said polypeptide comprises an amino acid sequence encoded by a nucleotide sequence that has been obtained by modifying SEQ ID NO:2 or the complement thereof. According to a more preferred embodiment, the at least one polypeptide having a patchoulol and 7-epi-α-selinene synthase activity used in any of the above-described embodiments or encoded by the nucleic acid used in any of the above-described embodiments consists of an amino acid sequence that is a variant of SEQ ID NO:1 obtained by genetic engineering, i.e. an amino acid sequence encoded by a nucleotide sequence that has been obtained by modifying SEQ ID NO:2 or the complement thereof.

As used herein, the polypeptide is intended as a polypeptide or peptide fragment that encompasses the amino acid sequences identified herein, as well as truncated or variant polypeptides, provided that they keep their activity as defined above and that they share at least the defined percentage of identity with the corresponding fragment of SEQ ID NO:1.

Examples of variant polypeptides are naturally occurring proteins that result from alternate mRNA splicing events or form proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends can also be used in the methods of the invention. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of the invention.

According to another embodiment, the at least one polypeptide having a patchoulol and 7-epi-α-selinene synthase activity used in any of the above-described embodiments or encoded by the nucleic acid used in any of the above-described embodiments is isolated from *Valeriana jatamansi*.

An important tool to carry out the method of the invention is the polypeptide itself. A polypeptide having a patchoulol and 7-epi-α-selinene synthase activity and comprising an amino acid sequence at least 50% identical to SEQ ID NO:1 is therefore another object of the present invention.

According to a preferred embodiment, the polypeptide is capable of producing patchoulol and 7-epi-α-selinene as the major products. According to an even more preferred embodiment, patchoulol and 7-epi-α-selinene represent altogether at least 50%, preferably at least 60%, preferably at least 70%, preferably at least 80%, preferably at least 90% of the product produced by the polypeptide of the invention.

According to another embodiment of the invention, 7-epi-α-selinene is the major product and patchoulol is the second major product. For example, 7-epi-α-selinene can represent at least 20%, preferably at least 30%, preferably at least 34% of the product obtained by the method of the invention. As another example, patchoulol can represent at least 10%, preferably at least 15%, preferably at least 16% of the product obtained by the method of the invention.

According to another embodiment, the product of the polypeptide of the present invention further comprises at least one compound selected from the group consisting of germacrene A, α-guaiene, α-humulene, α-selinene, seychellene, α-patchoulene, α-bulnesene and (E)-nerolidol, these compounds being defined by the way of their structure as depicted in FIG. 1. In a more preferred embodiment, the product of the method of the present invention comprises all of these compounds.

According to a preferred embodiment, the polypeptide comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1. According to a more preferred embodiment, the polypeptide comprises the amino acid sequence SEQ ID NO:1. According to an even more preferred embodiment, the polypeptide consists of SEQ ID NO:1.

According to another preferred embodiment, the polypeptide comprises an amino acid sequence that is a variant of SEQ ID NO:1 obtained by genetic engineering. In other terms, said polypeptide comprises an amino acid sequence encoded by a nucleotide sequence that has been obtained by modifying SEQ ID NO:2 or the complement thereof. According to a more preferred embodiment, the polypeptide having a patchoulol and 7-epi-α-selinene synthase activity consists of an amino acid sequence that is a variant of SEQ ID NO:1 obtained by genetic engineering, i.e. an amino acid sequence encoded by a nucleotide sequence that has been obtained by modifying SEQ ID NO:2 or the complement thereof.

According to another embodiment, the polypeptide is isolated form *Valeriana jatamansi*.

As used herein, the polypeptide is intended as a polypeptide or peptide fragment that encompasses the amino acid sequences identified herein, as well as truncated or variant polypeptides, provided that they keep their activity as defined above and that they share at least the defined percentage of identity with the corresponding fragment of SEQ ID NO:1.

Examples of variant polypeptides are naturally occurring proteins that result from alternate mRNA splicing events or form proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention.

Polypeptide variants resulting from a fusion of additional peptide sequences at the amino and carboxyl terminal ends are also encompassed by the polypeptides of the invention. In particular such a fusion can enhance expression of the polypeptides, be useful in the purification of the protein or improve the enzymatic activity of the polypeptide in a desired environment or expression system. Such additional peptide sequences may be a signal peptide, for example. Accordingly, the present invention encompasses variants of the polypeptides of the invention, such as those obtained by fusion with other oligo- or polypeptides and/or those which are linked to signal peptides. Polypeptides resulting from a fusion with another functional protein, such as another protein from the terpene biosynthesis pathway, are also encompassed by the polypeptides of the invention.

As mentioned above, the nucleic acid encoding the polypeptide of the invention is a useful tool to modify non-human host organisms or cells intended to be used when the method is carried out in vivo.

A nucleic acid encoding a polypeptide according to any of the above-described embodiments is therefore also an object of the present invention.

According to a preferred embodiment, the nucleic acid comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2 or the complement thereof. According to a more preferred embodiment, the nucleic acid comprises the nucleotide sequence SEQ ID NO:2 or the complement thereof. According to an even more preferred embodiment, the nucleic acid consists of SEQ ID NO:2 or the complement thereof.

According to another embodiment, the nucleic acid is isolated from *Valeriana jatamansi*.

The nucleic acid of the invention can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of the invention also encompass certain isolated nucleotide sequences including those that are substantially free from contaminating endogenous material. The nucleic acid of the invention may be truncated, provided that it encodes a polypeptide encompassed by the present invention, as described above.

According to a more preferred embodiment, the at least one nucleic acid according to any of the above embodiments comprises a nucleotide sequence that has been obtained by modifying SEQ ID NO:2 or the complement thereof. Preferably said nucleic acid consists of a nucleotide sequence that has been obtained by modifying SEQ ID NO:2 or the complement thereof.

The nucleic acids comprising a sequence obtained by mutation of SEQ ID NO:2 or the complement thereof are encompassed by the invention, provided that the sequences they comprise share at least the defined percentage of identity with the corresponding fragments of SEQ ID NO:2 or the complement thereof and provided that they encode a polypeptide having a patchoulol and 7-epi-α-selinene synthase activity, as defined in any of the above embodiments.

Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention.

Another important tool for transforming host organisms or cells suitable to carry out the method of the invention in vivo is an expression vector comprising a nucleic acid according to any embodiment of the invention. Such a vector is therefore also an object of the present invention.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of the invention operably linked to at least one regulatory sequence, which controls the initiation and/or termination of the transcription and/or translation, such as a transcriptional promoter, operator or enhancer, or an mRNA ribosomal binding site and, optionally, including at least one selection marker. Nucleotide sequences are "operably linked" when the regulatory sequence functionally relates to the nucleic acid of the invention.

The expression vectors of the present invention may be used in the methods for preparing a genetically transformed host organism and/or cell, in host organisms and/or cells harboring the nucleic acids of the invention and in the methods for producing or making polypeptides having a patchoulol and 7-epi-α-selinene synthase activity, as disclosed further below.

Recombinant non-human host organisms and cells transformed to harbor at least one nucleic acid of the invention so that it heterologously expresses or over-expresses at least one polypeptide of the invention are also very useful tools to carry out the method of the invention. Such non-human host organisms and cells are therefore another object of the present invention.

A nucleic acid according to any of the above-described embodiments can be used to transform the non-human host organisms and cells and the expressed polypeptide can be any of the above-described polypeptides.

Non-human host organisms of the invention may be any non-human multicellular or unicellular organisms. In a preferred embodiment, the non-human host organism is a plant, a prokaryote or a fungus. Any plant, prokaryote or fungus is suitable to be transformed according to the present invention. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism is a microorganism. Any microorganism is suitable for the present invention, but according to an even more preferred embodiment said microorganism is a bacteria or yeast. Most preferably, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Preferred higher eukaryotic cells are plant cells or fungal cells.

The term "transformed" refers to the fact that the host was subjected to genetic engineering to comprise one, two or more copies of each of the nucleic acids required in any of the above-described embodiment. Preferably the term "transformed" relates to hosts heterologously expressing the polypeptides encoded by the nucleic acid with which they are transformed, as well as over-expressing said polypeptides. Accordingly, in an embodiment, the present invention provides a transformed organism, in which the polypeptides are expressed in higher quantity than in the same organism not so transformed.

There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., *Cloning Vectors: A Laboratory Manual,* 1985, Elsevier, New York and Sambrook et al., *Molecular Cloning: A Laboratory Manual,* 2$^{nd}$ edition, 1989, Cold Spring Harbor Laboratory Press. Cloning and expression vectors for higher plants and/or plant cells in particular are available to the skilled person. See for example Schardl et al. *Gene* 61: 1-11, 1987.

Methods for transforming host organisms or cells to harbor transgenic nucleic acids are familiar to the skilled person. For the creation of transgenic plants, for example, current methods include: electroporation of plant protoplasts, liposome-mediated transformation, agrobacterium-mediated transformation, polyethylene-glycol-mediated transformation, particle bombardement, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection.

In order to carry out the method for producing patchoulol and 7-epi-α-selinene in vitro, as exposed herein above, it is very advantageous to provide a method of making at least one polypeptide having a patchoulol and 7-epi-α-selinene synthase activity as described in any embodiment of the invention. Therefore, the invention provides a method for producing at least one polypeptide according to any embodiment of the invention comprising a) culturing a non-human host organism or cell transformed with the expression vector of the invention, so that it harbors a nucleic acid according to the invention and expresses or over-expresses a polypeptide of the invention;
b) isolating the polypeptide from the non-human host organism or cell cultured in step a).

According to a preferred embodiment, said method further comprises, prior to step a), transforming a non-human host organism or cell with the expression vector of the invention, so that it harbors a nucleic acid according to the invention and expresses or over-expresses the polypeptide of the invention.

A nucleic acid according to any of the above-described embodiments can be used.

Transforming and culturing of the non-human host organism or cell can be carried out as described above for the method of producing patchoulol and 7-epi-α-selinene in vivo. Step b) may be performed using any technique well known in the art to isolate a particular polypeptide from an organism or cell.

A "polypeptide variant" as referred to herein means a polypeptide having a patchoulol and 7-epi-α-selinene synthase activity and being substantially homologous to the polypeptide according to any of the above embodiments, but having an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, *Biochemistry,* 1983, Addison-Wesley Pub. Co. The effects of such substitutions can be calculated using substitution score matrices such a PAM-120, PAM-200, and PAM-250 as discussed in Altschul, *J. Mol. Biol.,* 1991, 219, 555-565. Other such conservative substitutions, for example substitutions of entire regions having similar hydrophobicity characteristics, are well known.

Naturally occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the polypeptides of the invention may be used to attain for example desired enhanced or reduced enzymatic activity, modified regiochemistry or stereochemistry, or altered substrate utilization or product distribution, increased affinity for the substrate, improved specificity for the production of one or more desired compounds, increased velocity of the enzyme reaction, higher activity or stability in a specific environment (pH, temperature, solvent, etc), or improved expression level in a desired expression system. A variant or site directed mutant may be made by any method known in the art. Variants and derivatives of native polypeptides can be obtained by isolating naturally-occurring variants, or the nucleotide sequence of variants, of other or same plant lines or species, or by artificially programming mutations of nucleotide sequences coding for the polypeptides of the invention. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides. Fusion polypeptides encompassed by the invention also comprise fusion polypeptides resulting from a fusion of other functional proteins, such as other proteins from the terpene biosynthesis pathway.

Therefore, in an embodiment, the present invention provides a method for preparing a variant polypeptide having a patchoulol and 7-epi-α-selinene synthase activity, as described in any of the above embodiments, and comprising the steps of:
(a) selecting a nucleic acid according to any of the embodiments exposed above;
(b) modifying the selected nucleic acid to obtain at least one mutant nucleic acid;
(c) transforming host cells or unicellular organisms with the mutant nucleic acid sequence to express a polypeptide encoded by the mutant nucleic acid sequence;
(d) screening the polypeptide for at least one modified property; and,
(e) optionally, if the polypeptide has no desired variant patchoulol and 7-epi-α-selinene synthase activity, repeating the process steps (a) to (d) until a polypeptide with a desired variant patchoulol and 7-epi-α-selinene synthase activity is obtained;
(f) optionally, if a polypeptide having a desired variant patchoulol and 7-epi-α-selinene synthase activity was identified in step d), isolating the corresponding mutant nucleic acid obtained in step (c).

According to a preferred embodiment, the variant polypeptide prepared is capable of producing patchoulol and 7-epi-α-selinene as the major products. According to an even more preferred embodiment, patchoulol and 7-epi-α-selinene represent altogether at least 50%, preferably at least 60%, preferably at least 70%, preferably at least 80%, preferably at least 90% of the product produced by the variant polypeptide prepared.

According to another embodiment of the invention, 7-epi-α-selinene is the major product and patchoulol is the second major product. For example, 7-epi-α-selinene can represent at least 20%, preferably at least 30%, preferably at least 34% of the product obtained with the variant polypeptide prepared. As another example, patchoulol can represent at least 10%, preferably at least 15%, preferably at least 16% of the product obtained with the variant polypeptide prepared.

According to another embodiment, the product of the variant polypeptide prepared further comprises at least one compound selected from the group consisting of germacrene A, α-guaiene, α-humulene, α-selinene, seychellene, α-patchoulene, α-bulnesene and (E)-nerolidol, these compounds being defined by the way of their structure as depicted in FIG. 1. In a more preferred embodiment, the product of the variant polypeptide prepared comprises all of these compounds.

In step (b), a large number of mutant nucleic acid sequences may be created, for example by random mutagenesis, site-specific mutagenesis, or DNA shuffling. The detailed procedures of gene shuffling are found in Stemmer, DNA shuffling by random fragmentation and reassembly: in vitro recombination for molecular evolution. Proc Natl Acad Sci USA., 1994, 91(22): 10747-1075. In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

Accordingly, the polypeptide comprising SEQ ID NO:1 may be recombined with any other sesquiterpene synthase encoding nucleic acids, for example isolated from an organism other than *Valeriana jatamansi*. Thus, mutant nucleic acids may be obtained and separated, which may be used for transforming a host cell according to standard procedures, for example such as disclosed in the present examples.

In step (d), the polypeptide obtained in step (c) is screened for at least one modified property, for example a desired modified enzymatic activity. Examples of desired enzymatic activities, for which an expressed polypeptide may be screened, include enhanced or reduced enzymatic activity, for example as measured by $K_M$ or $V_{max}$ value, modified regio-chemistry or stereochemistry and altered substrate utilization or product distribution. The screening of enzymatic activity can be performed according to procedures familiar to the skilled person and those disclosed in the present examples.

Step (e) provides for repetition of process steps (a)-(d), which may preferably be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person.

All the publications mentioned in this application are incorporated by reference to disclose and describe the methods and/or materials in connection with which the publications are cited.

SPECIFIC EMBODIMENTS OF THE INVENTION OR EXAMPLES

Figure 1:
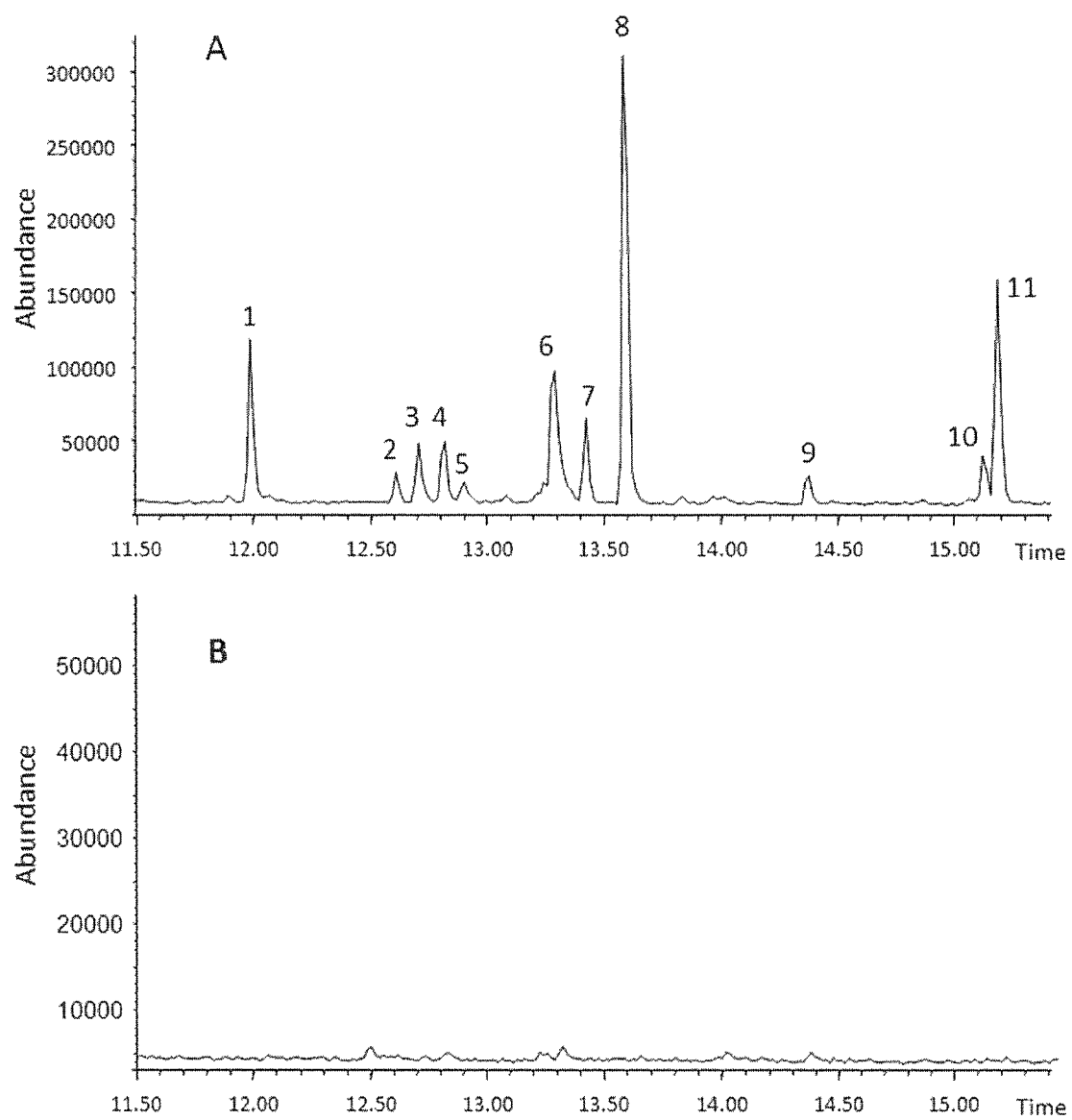
FIG. 1: Total ion chromatograms of GC-MS analysis of the sesquiterpene products generated by the patchoulol and 7-epi-α-selinene synthase of the present invention (SEQ ID NO:1) (A) and profile obtained with a negative control (B). The peaks marked with numbers were identified as sesquiterpenes: β-elemene (degradation product of (+)-germacrene A) (1); α-guaiene (2); seychellene (3); α-humulene (4); α-patchoulene (5); α-selinene (6); α-bulnesene (7); 7-epi-α-selinene (8); (E)-nerolidol (9); unidentified sesquiterpene alcohol (10); patchoulol (11).
Figure 2:
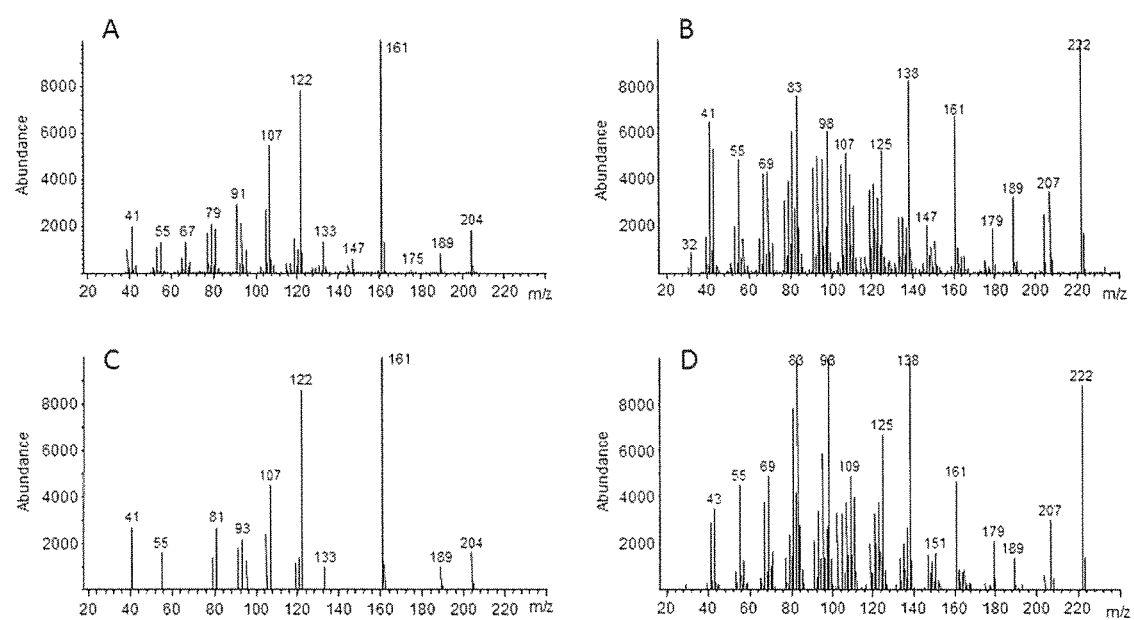
FIG. 2: Mass spectra of the two major products of the patchoulol and 7-epi-α-selinene synthase of the invention (SEQ ID NO:2) (peak 8 and peak 11 in FIG. 1 (A and B respectively)) and comparison to the mass spectra of authentic 7-epi-α-selinene and patchoulol (C and D respectively).
Figure 3:
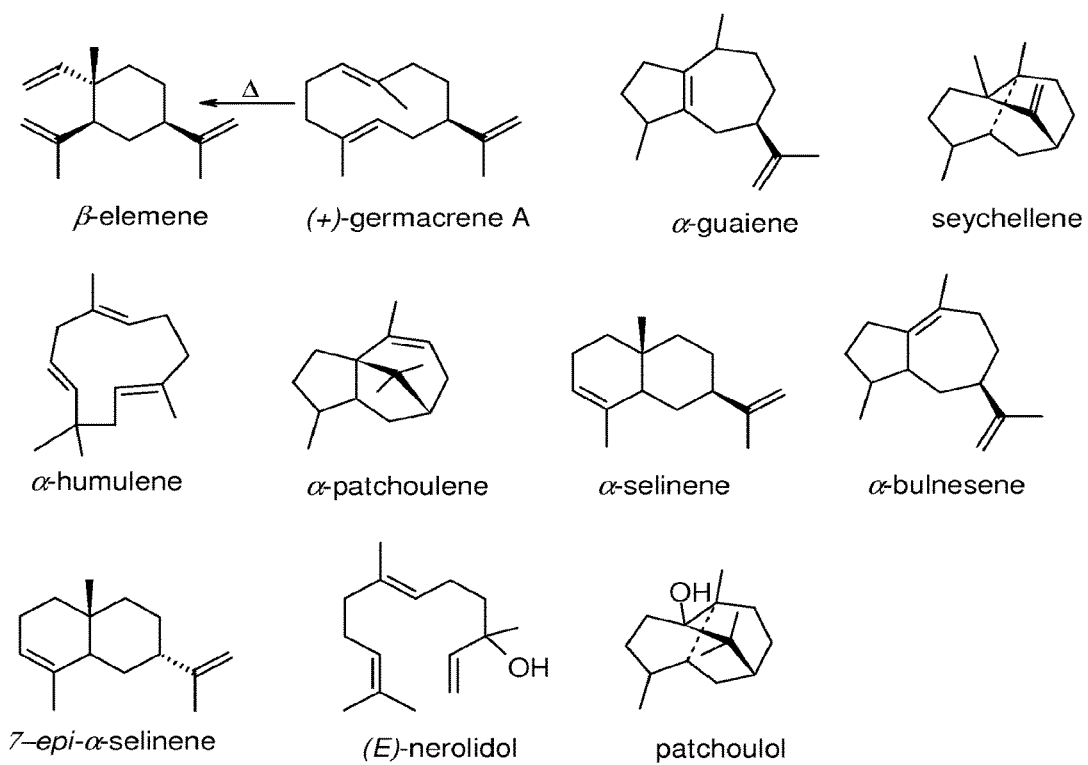
FIG. 3: Structure of the sesquiterpenes produced by the patchoulol and 7-epi-α-selinene synthase of the invention (SEQ ID NO:2).

The invention will now be described in further detail by way of the following Examples.

EXAMPLE 1

Isolation of a Sesquitepene Synthase cDNA from *Valeriana jatamansi* Roots

*Valeriana jatamansi* (synonym: *Valeriana walichii*) plants were obtained from B & T World Seeds (Paguignan, Aigues-Vives, France). The plants were cultivated in a green house at minimal temperature of 14° C. Rhizomes, young and mature roots were collected separately and immediately frozen in liquid nitrogen. The material was crushed and grinded to a fine powder in liquid nitrogen using a mortar and pestle. Total RNA was extracted using the CONCERT™ Plant RNA Reagent from Invitrogen following the manufacturer instruction except for the isopropanol precipitation which was replaced by a 2M LiCl precipitation. The quality of the RNA was evaluated on an agarose gel by verifying the integrity of the ribosomal RNA bands. The mRNA was purified from the total RNA by oligodT-cellulose affinity chromatography using the FASTTRACK® 2.0 mRNA isolation Kit (Invitrogen) following the manufacturer's instructions.

Degenerated oligonucleotides were designed to conserved motifs observed in alignments of the amino acid sequences of plant sesquiterpene synthases (Deguerry et al, 2006, Arch Biochem Biophys. 454(2), 123-36). RT-PCR with these sesquiterpene synthases-specific oligonucleotides were performed using the Qiagen OneStep RT-PCR Kit and an Eppendorf Mastercycler gradient thermal cycler. Typical reaction mixtures contain 10 μl 5× Qiagen OneStep RT-PCR buffer, 200 μM each dNTP, 0.4 μM each primer, 2 μl Qiagen OneStep RT-PCR Enzyme Mix, 1 μl RNASIN® Ribonuclease Inhibitor (Promega Co.) and 1 μg total RNA in a final volume of 50 μl. The thermal cycler conditions were: 30 min at 50° C. (reverse transcription); 15 min at 95° C. (DNA polymerase activation); 35 cycles of 30 sec at 94° C., 30 sec at 41 to 51° C. and 1 min at 72° C. The sizes of the PCR products were evaluated on a 1.2% agarose gel. The bands corresponding to the expected size were excised from the gel, purified using the QIAQUICK® Gel Extraction Kit (Qiagen) and cloned in the pCR®2.1-TOPO vector using the TOPO TA cloning Kit (Invitrogen). Inserted cDNAs were then subject to DNA sequencing and the sequence compared against the GenBank non-redundant protein database (NCBI) using the BLASTX algorithm (Altschul et al 1990, J. Mol. Biol. 215, 403-410). The combination of the forward primer TpsCF2 (SEQ ID NO:3) (5'-GGGA(A/T)(A/T)G(A/T)(A/T/G/C)(A/T)(C/T/G)GTTGAA(T/G)(T/G)TT-ATTTTTGG-3') and the reverse primer TpsCR3 (SEQ ID NO:4) (5'-GT(A/T)(C/G)CGTG(A/T/G/C/)G(A/C/T)GTCGTA(A/C/T)G(T/G)GTCATC-3') provided a fragment of 81 by presenting sequence homology with known plant sesquiterpene synthases.

A combination of 3' and 5' Rapid Amplification of cDNA Ends (RACE) was then used to obtain the full-length sequence of the cDNA corresponding to this fragment. For the 3'RACE, two sens oligonucleotides were deduced from the 81 by sequence obtained by RT-PCR: 20-3R1 (SEQ ID NO:5) and 20-3R2 (SEQ ID NO:6). An adaptor-ligated double stranded cDNA was prepared using the MARATHON™ cDNA Amplification Kit (Clontech) following the manufacturer's protocol. This cDNA was prepared from mRNA purified from *V. jatamansi* rhizome total RNA. Typical RACE reaction mixtures contain, in a final volume of 50 μl, 5 μl 10× PCR Reaction Buffer (Clontech), 200 μM each dNTP, 1 μl ADVANTAGE® 2 Polymerase Mix, 200 nM each primer and 5 μl of 250 fold diluted cDNA. Amplification was performed on an Eppendorf Mastercycler gradient thermal cycler. The thermal Cycling conditions were as follows: 1 min at 94° C., 5 cycles of 5 sec at 94° C. and 3 min at 72° C., 5 cycles of 5 sec at 94° C. and 3 min at 70° C., 20 cycles of 5 sec at 94° C. and 3 min at 68° C. The amplification products were evaluated, sub-cloned, and the sequence analyzed as described above. The 3'-end of the cDNA was obtained after a first round amplification with the primer 20-3R1 and the AP1 primer (clontech) and a second round amplification with the primer 20-3R2 and the AP2 primer (Clontech).

Two reverse primers were deduced from the sequence obtained by 3'RACE: 20-5R1 (SEQ ID NO:7) and 20-5R2 (SEQ ID NO:8). The SMART™ RACE cDNA amplification Kit (Clontech) was used to prepare a 5'RACE-ready cDNA from *V. jatamansi* root total RNA. The 5'RACE was performed in 50 μl of 1× advantage 2 PCR buffer containing 200 μM dNTPs, 5 μl Universal Primer Mix (Clontech), 2 μM of the first gene specific primer (20-5R1), 2.5 μl 5'RACE-ready cDNA and 1 μl ADVANTAGE® 2 Polymerase Mix. A second round of amplification was performed in the same condition with 1 μl of the first amplification, the nested gene specific primer (20-5R2) and the Nested Universal primer (Clontech). The temperature cycling condition and DNA fragment analysis were as described above for the 3'RACE.

The combination of 3' and 5'-RACE allowed the reconstitution of the full-length sequence of a cDNA which was named ValR20 (SEQ ID NO:9). The deduced amino acid sequence (SEQ ID NO:10) showed homology with plant sesquiterpene synthases and contained typical terpene synthases amino acid motifs such as the DDxxD motif. The closest sequences were a vetispiradiene synthase amino acid sequence from *S. tuberosum* (49% identity) and a putative sesquiterpene synthase from *V. vinifera* (up to 46% identity).

EXAMPLE 2

Heterologous Expression and Characterization of ValR20 as a 7-epi-α-selinene and Patchoulol Synthase Two oligonucleotides, Val-R20-topo-start (SEQ ID NO:11) and Val-R20-stop (SEQ ID NO:12), where designed from the start and stop regions of ValR20 and used to amplify the full-length sequence of this cDNA. The Val-R20-topo-start was designed according to the CHAMPION™ pET Directional TOPO® Expression Kits (invitrogen). The amplification was performed with the Pfu DNA polymerase (Promega) from the 5'-RACE-Ready cDNA pool prepared with the Smart RACE cDNA amplification kit (clontech). The thermal cycling conditions were as follows: 2 min at 95° C.; 32 cycles of 5 sec at 94° C., 20 sec at 53° C. and 3 min at 72° C. The PCR products were purified on an agarose gel and eluted using the QIAQUICK® Gel Extraction Kit (Qiagen, Valencia, Calif.). The PCR product was ligated into the pET101 plasmid following the manufacturer protocol (Invitrogen). The constructs were verified by DNA sequencing. One clone, 504-ValR20 (SEQ ID NO:2), was selected for the subsequent heterologous expression and enzyme assay experiments. Compared to the sequences reconstituted from the RACE, the sequence of 504-ValR20 (SEQ ID NO:2) showed four nucleotide differences leading to three amino acid changes. The amino acid sequence encoded by 504-ValR20 is provided in SEQ ID NO:1.

The plasmid was transferred into BL21 STAR™ (DE3) *E coli* cells (Invitrogen). Single colonies of transformed cells were used to inoculate 5 mL LB medium. After reaching an OD of 0.3, the 5 mL cultures were used to inoculate 25 mL of LB medium. The cultures were incubated at 37° C. until reaching an OD of 0.5 and they were then transferred to a 20° C. incubator. After 1 hour equilibration, the expression of the proteins was induced by addition of 1 mM IPTG and the culture were incubated over-night at 20° C. The next day, the cells were collected by centrifugation, resuspended in 1 mL Extraction Buffer (50 mM MOPSO, pH 7.4, 1 mM DTT, 10% glycerol) and disrupted by sonication. The cell debris were sedimented by centrifugation 30 min at 18,000 g and the supernatant containing the soluble proteins was recovered.

The enzymatic assays were performed in Teflon sealed glass tubes using 250 μL protein extract in a final volume of 5 mL Extraction Buffer supplemented with 10 mM $MgCl_2$ and 100 to 250 μM farnesyl pyrophosphate (prepared as described by Keller and Thompson, J. Chromatogr 645(1), 161-167, 1993). The assays were overlaid with 3 mL pentane and the tubes incubated overnight at 30° C. The pentane phase was recovered and the medium extracted with a second volume of pentane. The combined pentane fractions were concentrated under nitrogen and analyzed by GC-MS on a Hewlett-Packard 6890N GC-quadrupole mass selective detector system, equipped with a 0.25 mm inner diameter by 30 m length DB-1MS (J&W Scientific) capillary column. The oven temperature was programmed from 50° C. (1 min hold) to 280° C. at 10° C./min. The carrier gas was He at a constant flow of 1 mL/min. The identity of the products was confirmed based on the concordance of the retention indexes and mass spectra of authentic standards when available or based on published data (Joulain and Koenig, 1998). Negative controls were performed with proteins obtained from *E coli* transformed with the pET101 plasmid without insert.

The recombinant enzyme (SEQ ID NO:1) was found to be a multiple product sesquiterpene synthase converting farnesyl-pyrophosphate to at least 11 products. The major product was 7-epi-α-selinene which accounted for 34.2% of the total sesquiterpene mixture. Patchoulol was the second most abound product of the enzyme (16.4%). Other sesquiterpene produced were germacrene A (12.2%), α-guaiene (2.4%), seychellene (4.6%), α-humulene (5.3%), α-patchoulene (2.4%), α-selinene (9.6%), α-bulnesene (6.3%), (E)-nerolidol (2.5%) and an unidentified sesquiterpene alcohol (4.1%).

What is claimed is:

1. A method for producing a mixture of terpenes comprising one or more of patchoulol and 7-epi-α-selinene comprising
   a) contacting FPP with at least one polypeptide having sesquiterpene synthase activity and comprising an amino acid sequence at least 90% identical to SEQ ID NO:1 to produce a mixture of terpenes;
   b) optionally, isolating the mixture of terpenes comprising one or more of patchoulol and 7-epi-α-selinene produced in step a).

2. The method of claim 1, wherein step a) comprises cultivating a non-human host organism or cell capable of producing FPP comprising at least one polypeptide having sesquiterpene synthase activity comprising an amino acid sequence at least 90% identical to SEQ ID NO:1, under conditions conducive to the production of the mixture of terpenes comprising one or more of patchoulol and 7-epi-α-selinene.

3. The method of claim 2, which further comprises, prior to step a), transforming a non-human host organism or cell capable of producing FPP with at least one nucleic acid encoding a polypeptide comprising an amino acid sequence at least 90% identical to SEQ ID NO:1 and having a sesquiterpene synthase activity, so that said organism or cell expresses said polypeptide.

4. The method of claim 3, wherein the nucleic acid comprises a nucleotide sequence at least 90% identical to SEQ ID NO:2 or the complement thereof, or the nucleic acid comprises or consists of the nucleotide sequence of SEQ ID NO:2 or the complement thereof.

5. The method of claim 2, wherein the non-human host organism or cell is a plant, a prokaryote, a fungus, a microorganism, a bacteria, a yeast, a plant cell or a fungal cell.

6. The method of claim 5, wherein the bacteria is *E. coli* and the yeast is *Saccharomyces cerevisiae*.

7. The method of claim 1. wherein the polypeptide comprises an amino acid sequence at least 95%, 98% or 100% identical to SEQ ID NO:1.

\* \* \* \* \*